US010636515B2

(12) United States Patent
Utsunomiya et al.

(10) Patent No.: US 10,636,515 B2
(45) Date of Patent: Apr. 28, 2020

(54) MEDICAL OR HEALTH INFORMATION SEARCH SUPPORT APPARATUS AND MEDICAL OR HEALTH INFORMATION SEARCH SUPPORT SYSTEM

(71) Applicant: TOSHIBA MEDICAL SYSTEMS CORPORATION, Otawara-Shi (JP)

(72) Inventors: Kazuki Utsunomiya, Otawara (JP); Satoshi Ikeda, Yaita (JP); Longxun Piao, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 923 days.

(21) Appl. No.: 14/294,502

(22) Filed: Jun. 3, 2014

(65) Prior Publication Data
US 2014/0278558 A1 Sep. 18, 2014

Related U.S. Application Data

(63) Continuation of application No. PCT/JP2013/061649, filed on Apr. 19, 2013.

(30) Foreign Application Priority Data

Apr. 19, 2012 (JP) ................................ 2012-096029
Apr. 19, 2013 (JP) ................................ 2013-088150

(51) Int. Cl.
*G16H 10/60* (2018.01)
*G06F 19/00* (2018.01)
(Continued)

(52) U.S. Cl.
CPC ........... *G16H 10/60* (2018.01); *G06F 19/324* (2013.01); *G06F 19/3456* (2013.01);
(Continued)

(58) Field of Classification Search
CPC ...... G06F 19/345; G06F 19/322; G06F 19/22; G06F 19/3443; G06F 19/326;
(Continued)

(56) References Cited

U.S. PATENT DOCUMENTS

2003/0167189 A1* 9/2003 Lutgen .................. G06F 19/322
705/3
2005/0278196 A1* 12/2005 Potarazu ................ G06Q 10/10
705/2

(Continued)

FOREIGN PATENT DOCUMENTS

CN 101398852 A 4/2009
CN 101529453 A 9/2009
(Continued)

OTHER PUBLICATIONS

International Search Report dated May 21, 2013 for PCT/JP2013/061649 filed on Apr. 19, 2013 with English Translation.
(Continued)

*Primary Examiner* — Jonathan Durant
(74) *Attorney, Agent, or Firm* — Oblon, McClelland, Maier & Neustadt, L.L.P.

(57) ABSTRACT

An apparatus for support in searching medical or health information receives a search keyword for searching for medical or health information of search target and a related disease name to analyze an administration information database in which administration information of prescriptions-treatments for patients and disease names are stored in association with each other. The apparatus acquires a related diseases name related to the disease name. Additionally, the apparatus can search the medical or health information for medical or health information stored in a medical or health information database on the basis of the search keyword and the related disease names display the medical or health information thus searched out.

13 Claims, 20 Drawing Sheets

(51) Int. Cl.
*G16H 50/70* (2018.01)
*G16H 50/20* (2018.01)
*G06Q 50/22* (2018.01)
*G06Q 10/06* (2012.01)

(52) U.S. Cl.
CPC ............ *G16H 50/20* (2018.01); *G16H 50/70* (2018.01); *G06Q 10/06* (2013.01); *G06Q 50/22* (2013.01)

(58) Field of Classification Search
CPC ...... G06F 19/324; G06F 19/325; G06F 16/00; G06F 16/285; G06Q 50/22; G06Q 50/24; G16H 10/60; G16H 50/20; G16H 50/30; G16H 70/20; G16H 70/60
See application file for complete search history.

(56) References Cited

U.S. PATENT DOCUMENTS

| | | | |
|---|---|---|---|
| 2010/0234236 A1* | 9/2010 | Cohen | G06F 19/3437 506/8 |
| 2010/0235378 A1* | 9/2010 | Armstrong | G06Q 10/10 707/769 |
| 2010/0312779 A1 | 12/2010 | Lim et al. | |

FOREIGN PATENT DOCUMENTS

| | | |
|---|---|---|
| CN | 102043813 A | 5/2011 |
| JP | 9-198396 A | 7/1997 |
| JP | 2000-293599 A | 10/2000 |
| JP | 2003-30327 A | 1/2003 |
| JP | 2010-505155 A | 2/2010 |

OTHER PUBLICATIONS

International Written Opinion dated May 21, 2013 for PCT/JP2013/061649 filed on Apr. 19, 2013.
Ly Bich Lam Ngoc et al., "A Searching System for Medical Information by Using Semantic Web Technology", IPSJ SIG Technical Report, vol. 2007, n.60, Jun. 14, 2007, pp. 39-45.
Combined Chinese Office Action and Search Report dated Jun. 23, 2016 in Patent Application No. 201380004286.4 (with English translation of Categories of Cited Documents).
International Preliminary Report on Patentability and Written Opinion dated Oct. 30, 2014 in PCT/JP2013/061649 filed on Apr. 19, 2013 (English translation only).
Office Action dated May 23, 2017 in Japanese Patent Application No. 2013-088150.

* cited by examiner

FIG. 3

DISEASE NAME TABLE

| DISEASE NAME ID | DISEASE NAME |
|---|---|
| 1 | ACUTE SINUSITIS |
| 2 | ACUTE BRONCHITIS |
| 3 | ACUTE BRONCHIOLITIS |
| 4 | ASTHMA |
| 5 | EXANTHEM SUBITEM |
| ... | ... |

FIG. 4

PRESCRIPTION-TREATMENT TABLE

| PRESCRIPTION ID | PRESCRIPRION-TREATMENT |
|---|---|
| 1 | aaa GRANULAR MEDICINE 50% |
| 2 | ddd TABLET 30 mg |
| 3 | eee COLLUNARIUM 15 mg |
| 4 | fff TABLET 15 mg |
| 5 | ccc TABLET 15 mg |
| 6 | ggg TABLET 200 |
| 7 | GRANULAR bbb EXTRACT (FOR MEDICAL USE) |
| ... | ... |

FIG. 5

MAP TABLE

| DISEASE NAME ID | PRESCRIPTION ID | DISEASE NAME | PRESCRIPTION-TREATMENT |
|---|---|---|---|
| 1 | 1 | ACUTE SINUSITIS | aaa GRANULAR MEDICINE 50% |
| 1 | 2 | ACUTE SINUSITIS | ddd TABLET 30 mg |
| 1 | 3 | ACUTE SINUSITIS | eee COLLUNARIUM 15 mg |
| 2 | 1 | ACUTE BRONCHITIS | aaa GRANULAR MEDICINE 50% |
| 2 | 4 | ACUTE BRONCHITIS | fff TABLET 15 mg |
| 2 | 5 | ACUTE BRONCHITIS | ccc TABLET 15 mg |
| 2 | 7 | ACUTE BRONCHITIS | GRANULAR bbb EXTRACT (FOR MEDICAL USE) |
| 2 | 6 | ACUTE BRONCHIOLITIS | ggg TABLET 200 |
| 3 | 1 | ASTHMA | aaa GRANULAR MEDICINE 50% |
| 4 | 7 | EXANTHEM SUBITEM | GRANULAR bbb EXTRACT (FOR MEDICAL USE) |
| ... | ... | ... | ... |

FIG.10

< SEARCH KEYWORD (MAIN DISEASE NAME) >

ACUTE BRONCHITIS

| DISEASE NAME | PRESCRIPRION-TREATMENT |
|---|---|
| ACUTE BRONCHITIS | aaa GRANULAR MEDICINE 50% |
| ACUTE BRONCHITIS | bbb TABLET 30 mg |
| ACUTE BRONCHITIS | ccc TABLET 15 mg |
| ACUTE BRONCHITIS | dd DECONGESTANT CAPSULE 24cp |
| ACUTE SINUSITIS | aaa GRANULAR MEDICINE 50% |
| ACUTE SINUSITIS | eee COLLUNARIUM 15 mg |
| ACUTE SINUSITIS | fff TABLET 15 mg |
| ASTHMA | ggg TABLET 30 mg |
| ... | ... |

ACUTE SINUSITIS

< SEARCH KEYWORD (RELATED DISEASE NAME) >

FIG. 14

| DISEASE NAME ID | CLASSIFICATION CODE | DISEASE NAME |
|---|---|---|
| 1 | 1001 | ACUTE SINUSITIS |
| 2 | 1020 | ACUTE BRONCHITIS |
| 3 | 1021 | ACUTE BRONCHIOLITIS |
| 4 | 1045 | ASTHMA |
| 5 | 208.2 | EXANTHEM SUBITEM |
| ... | ... | ... | ize
MEDICAL OR HEALTH INFORMATION SEARCH SUPPORT APPARATUS AND MEDICAL OR HEALTH INFORMATION SEARCH SUPPORT SYSTEM

CROSS-REFERENCE TO THE RELATED APPLICATION

This application is based on and claims the benefit of priority from International Application No. PCT/JP2013/061649, filed on Apr. 19, 2013, Japanese Patent Application No. 2012-096029, filed on Apr. 19, 2012 and Japanese Patent Application No. 2013-088150, filed on Apr. 19, 2013; the entire contents of which are incorporated herein by reference.

FIELD

Embodiments described herein relate generally to a medical or health information search support apparatus and a medical or health information search support system.

BACKGROUND

In recent years, as one kind of medical or health information, medical records of individual patients, for example, have been converted into electronic ones, and the electronic medical records stored in databases have been used widely.

Note that the electronic medical records is used as an example below. And the electronic medical records may be the electronic health records or the personal health records, for example.

The electronic medical records are used to store diagnostic information for individual patients, but are also secondarily usable as a database of cases, for example. In the secondary use, the electronic medical records are used to improve the quality of medical service through analysis of similar cases.

In the case of secondary use of the electronic medical records, a keyword to be searched for (for example, a disease name) is inputted, and medical records (the full-text documents of the electronic medical records) containing the inputted keyword are searched out from the database (Japanese Patent Application Publication No. 2000-293599).

However, even if patients have almost the same symptoms and receive almost the same prescriptions-treatments, different disease names are sometimes entered in the medical records depending on judgments by medical doctors. Such difference can be recognized as so-called "variations in disease name entry." For example, "acute bronchitis", "acute sinusitis" and "asthma" can be cited as one example of "variations in disease name entry".

In such a case, when "acute bronchitis" is inputted as a keyword for the secondary use of the electronic medical records, medical records entered with "acute bronchitis" can be searched out, but medical records entered not with "acute bronchitis" but with "acute sinusitis" or "asthma" cannot be searched out. In other words, this way of search is incapable of searching out electronic medical records containing disease names supposed to be medically related to the disease name inputted as the keyword.

Moreover, in terms of "variations," there is a case where two or more diseases having completely different disease names can be judged as being medically related to each other from the viewpoint of prescription-treatment, because for example the diseases are provided with almost the same prescription-treatment.

BRIEF DESCRIPTION OF THE DRAWINGS

FIG. 3 is an explanatory diagram illustrating a structure of an administration information database in the embodiment of the present invention.

FIG. 4 is an explanatory diagram illustrating the structure of the administration information database in the embodiment of the present invention.

FIG. 5 is an explanatory diagram illustrating the structure of the administration information database in the embodiment of the present invention.

FIG. 10 is an explanatory diagram illustrating the flow of search by using the structure of an administration information database in the first embodiment of the present invention.

FIG. 14 is a table presenting a relationship between a classification code and a disease name stored in a disease name/classification code storage unit in the third embodiment of the present invention.

DETAILED DESCRIPTION

Figure 1:
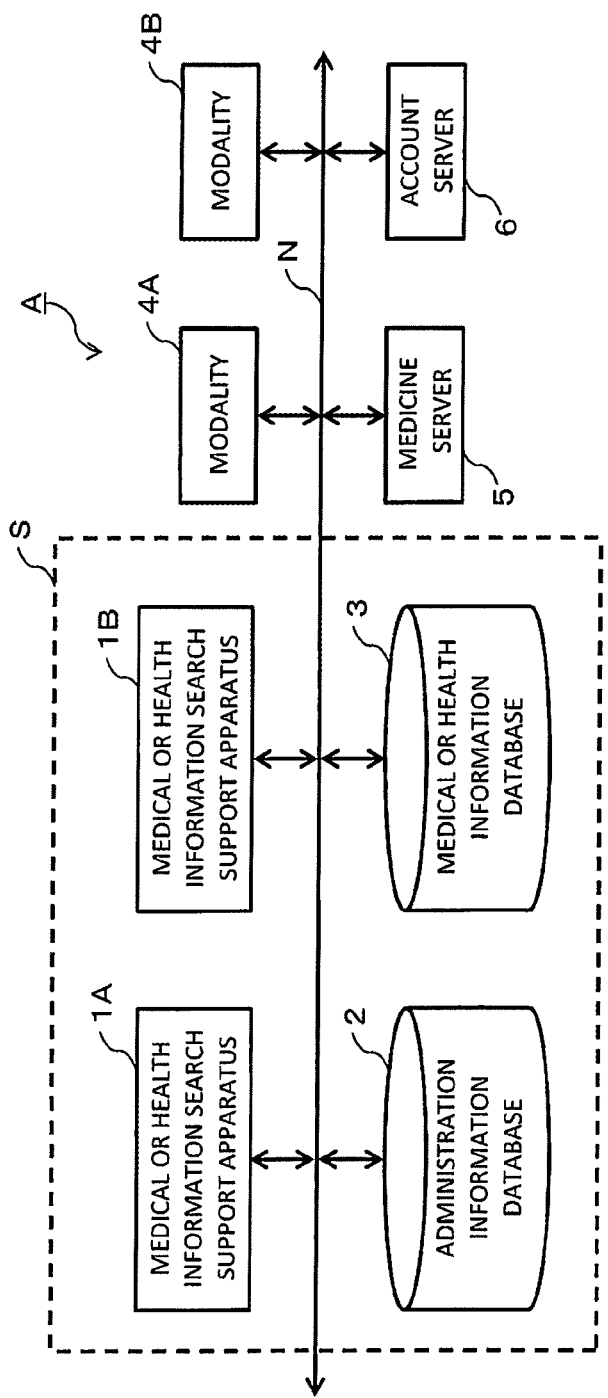
FIG. 1 is a block diagram illustrating an overall configuration of an in-hospital system including a medical or health information search support system in an embodiment of the present invention.

According to one embodiment, a medical or health information search support apparatus includes: an input unit to which a search keyword for searching for medical or health information of search target is inputted; a related disease name acquisition unit configured to analyze an administration information database in which administration information on a prescription-treatment for a patient and a disease name are stored in association with each other, and thereby to acquire a related disease name related to the disease name; a medical or health information search unit configured to search for medical or health information stored in a medical or health information database on the basis of the search keyword and the related disease name; and a display unit configured to display the medial or health information thus searched out.

According to another embodiment, a medical or health information search support apparatus includes: an input unit to which a prescription-treatment for a patient being a search keyword for searching for medical or health information of search target is inputted; a disease name acquisition unit configured to analyze an administration information database in which administration information on the prescription-treatment and a disease name are stored in association with each other, and acquire the disease name provided with the prescription-treatment; a medical or health information search unit configured to search for medical or health information stored in a medical or health information database on the basis of the disease name acquired by the disease name acquisition unit; and a display unit configured to display the medical or health information searched out.

According to another embodiment, a medical or health information search support system includes: an administration information database in which administration information on a prescription-treatment for a patient and a disease name are stored in association with each other; a medical or health information database in which medical or health information on the patient is stored; an input unit to which a search keyword for searching for medical or health information of search target is inputted; and a medical or health information search support apparatus including a related disease name acquisition unit configured to analyze the administration information database, and thereby to acquire a related disease name related to the disease name, a medical or health information search unit configured to search for medical or health information stored in the medical or health information database on the basis of the search keyword and the related disease name, and a display unit configured to display the medial or health information thus searched out.

According to another embodiment, a medical or health information search support system includes: an information terminal used by a person who refers to medical or health information, and at least including an input unit and a display unit; an administration information database in which administration information on a prescription-treatment for a patient and a disease name are stored in association with each other; a medical or health information database in which medical or health information on the patient is stored; and a search server including a reception unit configured to receive a search request for medical or health information of search target from the information terminal, a related disease name acquisition unit configured to analyze the administration information database, and thereby to acquire a related disease name related to the disease name, a medical or health information search unit configured to search for medical or health information stored in the medical or health information database on the basis of the search keyword and the related disease name, and a transmission unit configured to transmit the searched-out medial or health information to the information terminal.

Hereinafter, embodiments of the present invention will be described in detail with reference to the accompanying drawings.

First Embodiment

FIG. 1 is a block diagram illustrating an overall configuration of an in-hospital system A including a medical or health information search support system S in an embodiment of the present invention. The in-hospital system A is a system built in a medical institution, for example, and FIG. 1 illustrates one example of the system. The in-hospital system A includes medical or health information search support apparatuses 1, an administration information database 2, a medical or health information database 3, modalities 4, a medicine server 5 and an account server 6. These constituents of the in-hospital system A are connected to each other via a communication network N.

In addition, in the in-hospital system A, the medical or health information search support apparatuses 1, the administration information database 2 and the medical or health information database 3 constitute the medical or health information search support system S in the embodiment of the present invention. FIG. 1 illustrates the state where the plural medical or health information search support apparatuses 1 (medical information search support apparatuses 1A, 1B) and the plural modalities 4 (modalities 4A, 4B), for example, are connected to the communication network N. Note that one or more apparatuses of each type of the above constituents may be connected to the communication network N to form the medical or health information search support system S or the in-hospital system A. In addition, the numbers of apparatuses of the other types of constituents connected to the communication network N may be set freely.

Here, the medical or health information search support apparatuses 1A, 1B are collectively expressed as the "medical or health information search support apparatus 1" as needed, and the modalities 4A, 4B are similarly expressed as the "modality 4" as well.

The medical or health information search support apparatuses 1 are information terminals such for example as personal computers (PC), or multiple workstations connected to the in-hospital system A. The medical or health information search support apparatus 1 is an apparatus used by, for example, a medical doctor or the like who searches for electronic medical records (people searching for the electronic medical records by use of the medical or health information search support apparatus 1 are collectively referred to as a "user" as needed). Accordingly, the medical information search support apparatus 1 may be freely set to have any functions, form and the like, as long as the apparatus is able to allow the user to search for necessary electronic medical records. For example, it does not matter whether the connection method is wired or wireless, or whether the apparatus 1 is portable or stationary.

Figure 2:
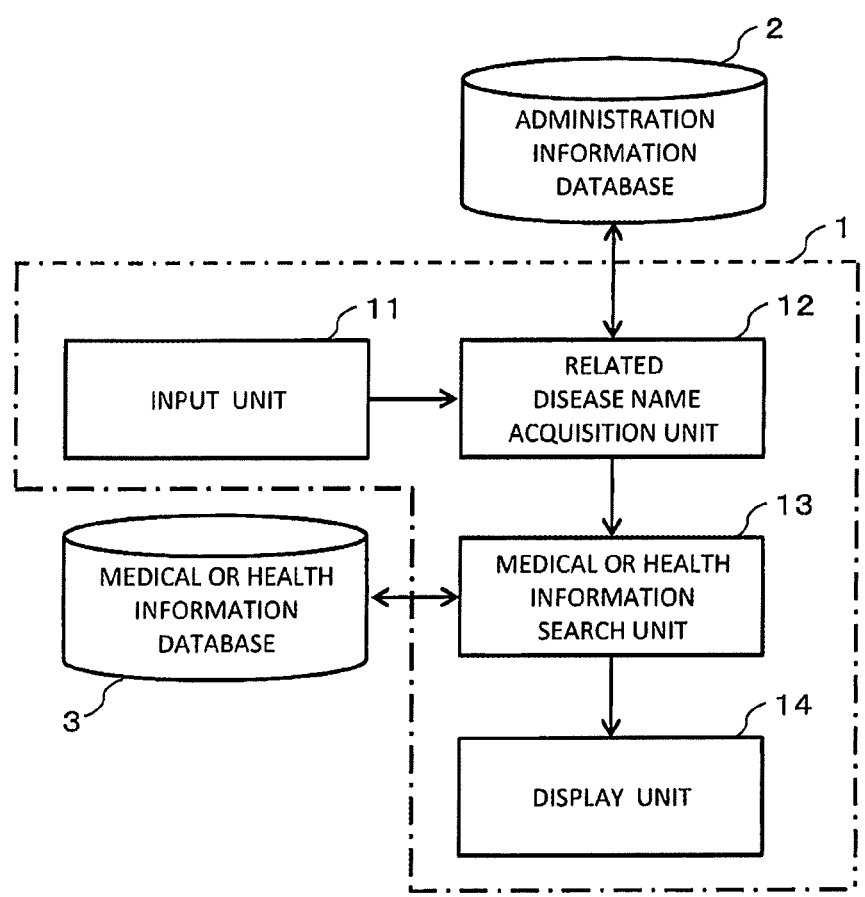
FIG. 2 is a block diagram illustrating an internal configuration of a medical or health information search support apparatus in the embodiment of the present invention.

FIG. 2 is a block diagram illustrating an internal configuration of the medical or health information search support apparatus 1 in the embodiment of the present invention. The medical or health information search support apparatus 1 includes an input unit 11, a related disease name acquisition unit 12, a medical or health information search unit 13 and a display unit 14.

The input unit 11 includes input devices such as a keyboard, a dial and the like on which a user of the medical or health information search support apparatus 1 performs various operations. An input signal is created based on the operations by the user, and is transmitted to a CPU via a bus, which are not illustrated in FIG. 2 but provided in the medical information search support apparatus 1. In the embodiment of the present invention, the input unit 11 is used by the user to input a disease name or the like when the user makes a search for electronic medical records as one kind of medical information.

In the search for the electronic medical records, the related disease name acquisition unit 12 searches for and acquires a related disease name from the later-described administration information database 2 on the basis of a prescription-treatment provided for the inputted disease name. Specifically, on the basis of the inputted disease name, the medical or health information search support system S in the embodiment of the present invention analyzes the prescription or treatment provided for the disease name and identifies a disease name provided with a prescription-treatment similar to the above prescription-treatment, as described layer.

To put it differently, the related disease name acquisition unit 12 searches for the disease name on the basis of the prescription-treatment, which is a search reverse to a search for a prescription-treatment on the basis of a disease name. Thus, the inputted disease name and the acquired related disease name are medically related to each other. Here, the "related disease name" is the name of a disease provided with substantially the same prescription or treatment as the prescription or treatment associated with the inputted disease name (provided for the inputted disease name).

The medical or health information search unit 13 searches for electronic medical records, for example, as one kind of medical or health information, and are stored in the medical or health information database 3, based on the related disease name identified by the related disease name acquisition unit through the search in the administration information database 2.

The display unit 14 is formed of, for example, a liquid crystal display. The display unit 14 displays information on the electronic medical records searched out from the medical or health information database 3 by the medical or health information search unit 13.

The following description is given by taking electronic medical records as an example of medical or health information of search target. Moreover, detailed description of actions taken by the constituents in an operation of searching electronic medical records will be provided together with explanation of a flow of the search.

The administration information database 2 stores administration information on a prescription (medicine name) or as treatment (a medical practice or the like conducted during a medical care or the like) provided to a patient, in association with the disease name of the patient. The administration information database 2 uses a file system, a database or a combined format of them, for example. When the administration information database 2 stores "acute bronchitis" as a disease name, for example, the prescription or treatment provided for the "acute bronchitis" is stored in the administration information database 2 while being associated with the disease name of "acute bronchitis." The foregoing related disease name acquisition unit 12 accesses the administration information database 2 and acquires the disease name related to the inputted disease name.

FIGS. 3 to 5 are explanatory diagrams illustrating a structure of the administration information database 2 in the embodiment of the present invention. FIG. 3 is a table for disease names. In the table, "disease name ID" and "disease name" are associated with each other. For instance, the disease name indicated by the "disease name ID" of "3" is "acute bronchiolitis." FIG. 4 is a table for prescriptions-treatments. In the table, "prescription ID" and "prescription-treatment" are associated with each other. For instance, the "prescription-treatment" in the case of the "prescription ID" of "2" is "ddd tablet 30 mg."

FIG. 5 is a map table in which the "disease name" presented in FIG. 3 and the "prescription-treatment" presented in FIG. 4 are stored in association with each other. This map table is provided to establish correspondence between the "disease name" and the "prescription-treatment" with each other. In addition, since specific prescriptions or treatments provided vary among disease names, the correspondence between the "disease name" and the "prescription-treatment" also varies naturally.

For example, the "prescription-treatment" of "aaa granular medicine 50%" is provided for all of "acute sinusitis," "acute bronchitis" and "asthma." Meanwhile, the "prescription-treatment" of any of "aaa granular medicine 50%," "ddd tablet 30 mg" and "eee collunarium 15 mg" is provided for (associated with) "acute sinusitis." Then, the "prescriptions-treatments" of "aaa granular medicine 50%," "fff tablet 15 mg," "ccc tablet 15 mg" and "granular bbb extract (for medical use)" are associated with "acute bronchitis." Here, each of the tables may have a preset structure or a structure to which data is added as needed according to cases of patients.

The medical or health information database 3 stores medical or health information containing information entered in medical records such as medical care information of individual patents. The medical or health information database 3 uses a file system, a database or a combined format of them, for example. The medical or health information search unit 13 of the medical or health information search support apparatus 1 accesses the medical or health information database 3 and searches for electronic medical records in each of which any of the inputted disease name and the related disease name is entered.

Figure 6:
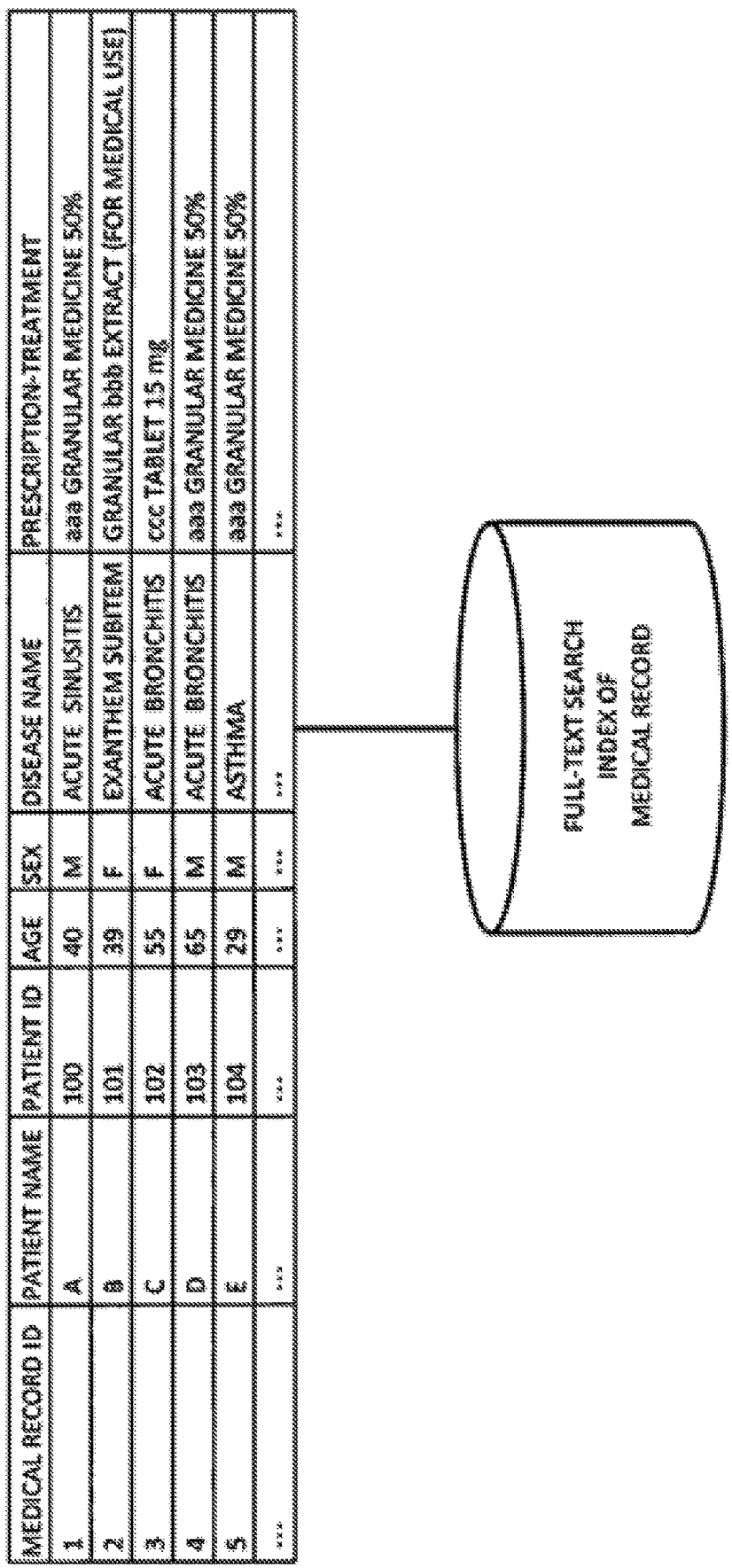
FIG. 6 is an explanatory diagram illustrating a structure of a medical or health information database in the embodiment of the present invention.

FIG. 6 is an explanatory diagram illustrating a structure of the medical or health information database 3 in the embodiment of the present invention. The medical or health information database 3 stores information entered in, for example, electronic medical records. The medical or health information database 3 stores not only bibliographic items of an electronic medical record such for example as a patient name and a patient ID, but also a "disease name," a "prescription-treatment" and the like, and a "medical record ID" is assigned to each electronic medical record.

Every time an electronic medical record is added or updated, the medical or health information database 3 is updated with the new information. In addition, various kinds of information updated in the medical or health information database 3 are also added to or updated in the administration information database 2. Such timely updating of the medical or health information database 3 and the administration information database 2 with the new information enables a more effective search for electronic medical records in terms of a main disease name or related disease name.

In addition, there are many cases where a search index is created in advance for a system for a full-text search on information of medical records of search target. In the example of the medical or health information database 3 illustrated in FIG. 6, a full-text search index of medical record documents is created in a disease name column.

Here, the column items in the table of the medical or health information database 3 in FIG. 6 are presented only for the illustrative purposes, and the medical or health information database 3 may store column items other than those presented in FIG. 6.

Figure 7:
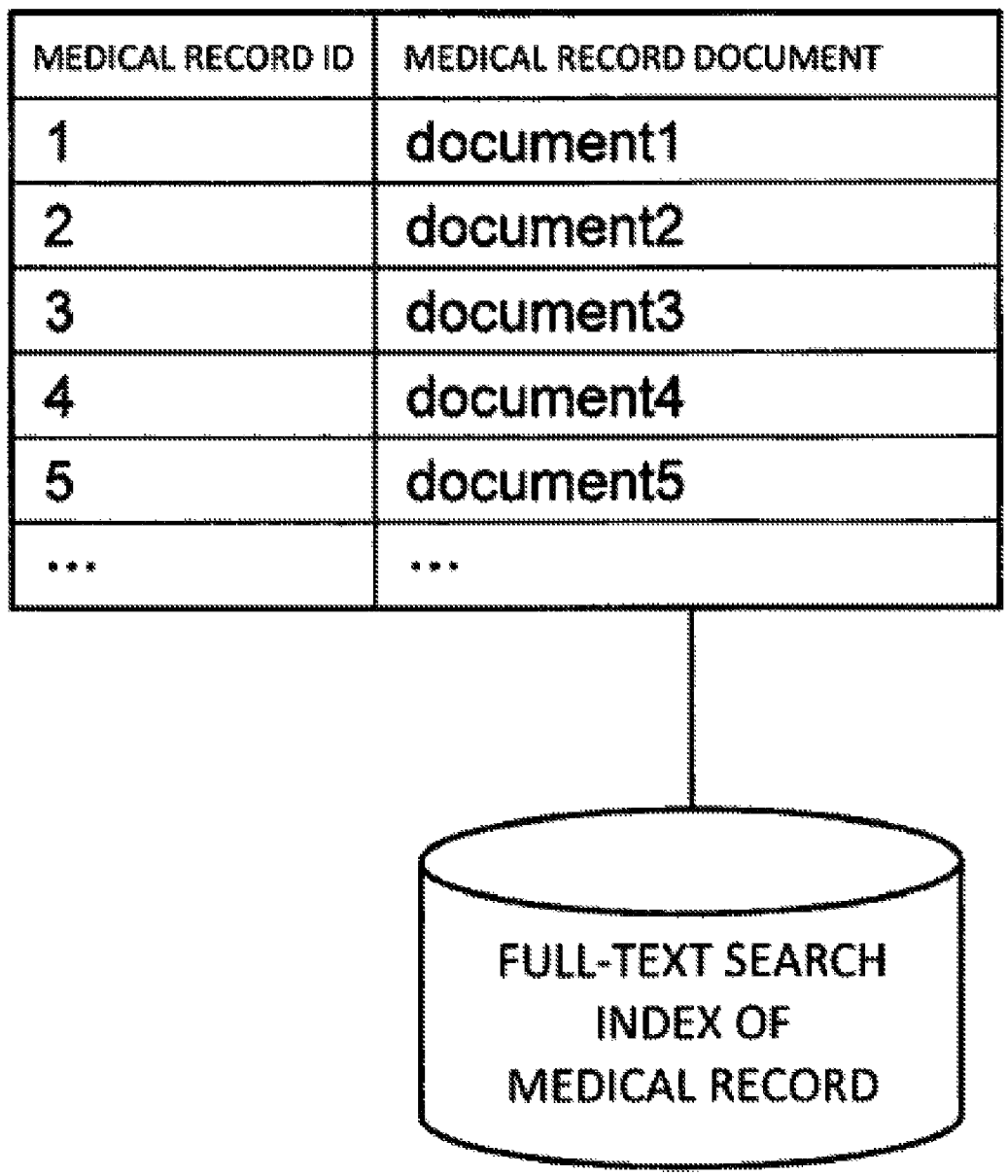
FIG. 7 is an explanatory diagram illustrating another structure of the medical or health information database in the embodiment of the present invention.
Figure 8:
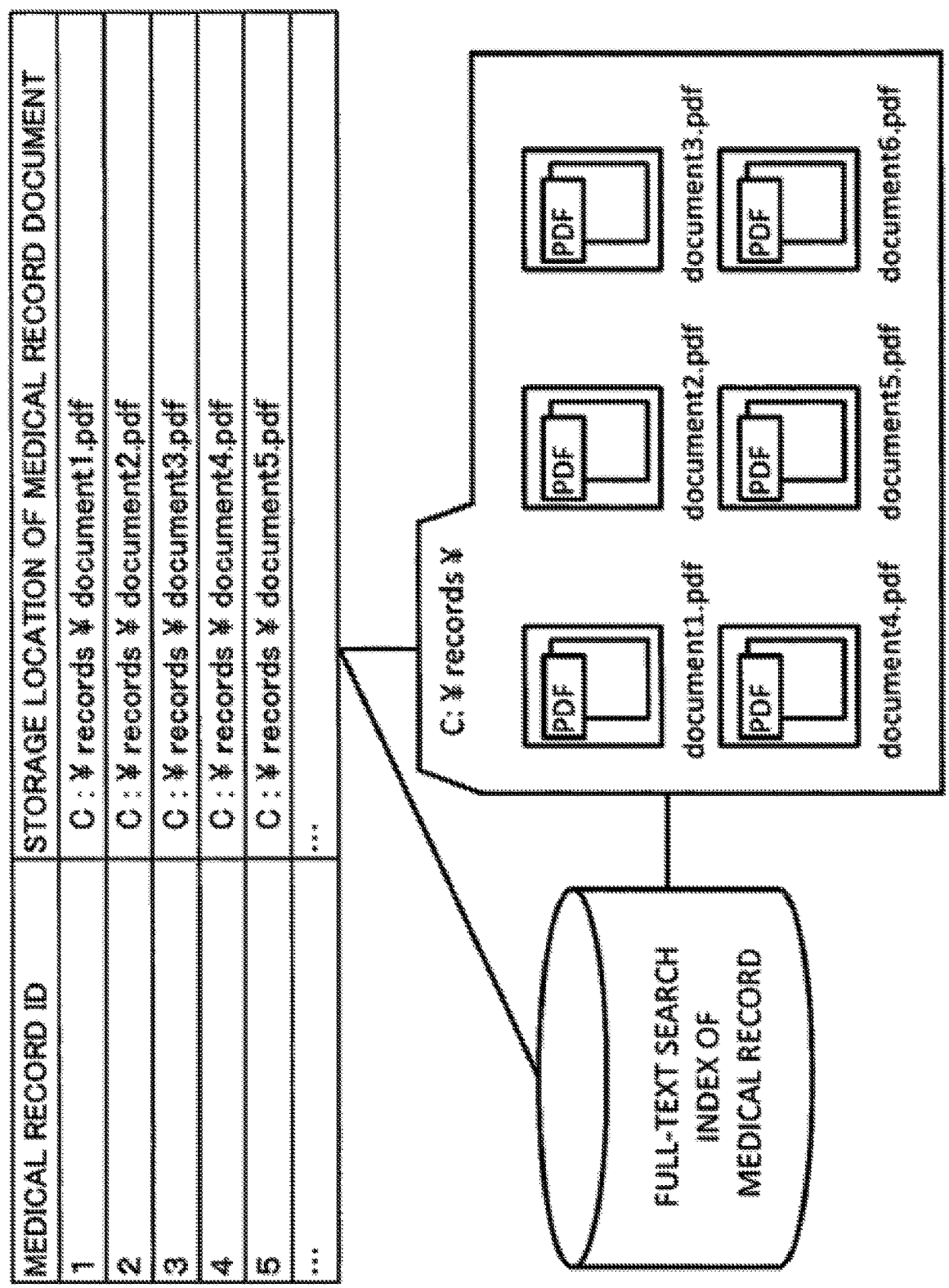
FIG. 8 is an explanatory diagram illustrating another structure of the medical or health information database in the embodiment of the present invention.

FIGS. 7 and 8 are explanatory diagrams illustrating other structures of the medical or health information database 3 in the embodiment of the present invention. In a table of the database illustrated in FIG. 7, information pieces entered in each medical record are collectively held as a medical record document. A table of the database illustrated in FIG. 8 presents a structure in which medical records are stored in a file system and information concerning the medical records is stored in the table of the database.

Here, any of the structures illustrated in FIGS. 6 to 8 can be employed for the medical or health information database 3. In this connection, for a full-text search for electronic medical records, it is necessary to scan the full text of each electronic medical record and to create an index in advance. The index creation is made prior to the search. The index creation for newly added electronic medical records is made at set timing such as every time a record is added, or when a predetermined number of records are added.

The modality 4 is a medical diagnostic imaging apparatus such as an X-ray CT (computed tomography) scanner or a magnetic resonance imaging (MRI), for example, and is an instrument for acquiring (capturing an image of) internal information of a patient.

The medicine server 5 is a server for managing administration of a medicine prescribed for a patient by a medical doctor through a medical care service, for example. The account server 6 is a server for managing the accounting of a fee for a medical service to be charged to a patient based on the medical record.

The communication network N connects the constituents in the in-hospital system A such as the medical or health information search support apparatuses 1, the administration information database 2, the medical or health information database 3 and the modalities 4 to each other, and enables the constituents to exchange information on electronic medical records and medical image information therebetween, for example. Examples of the communication network N include networks such as a local area network (LAN) and the Internet. Communication standards employed in the communication network N may be any standards, including Digital Imaging and Communication in Medicine (DICOM) and the like.

Figure 9:
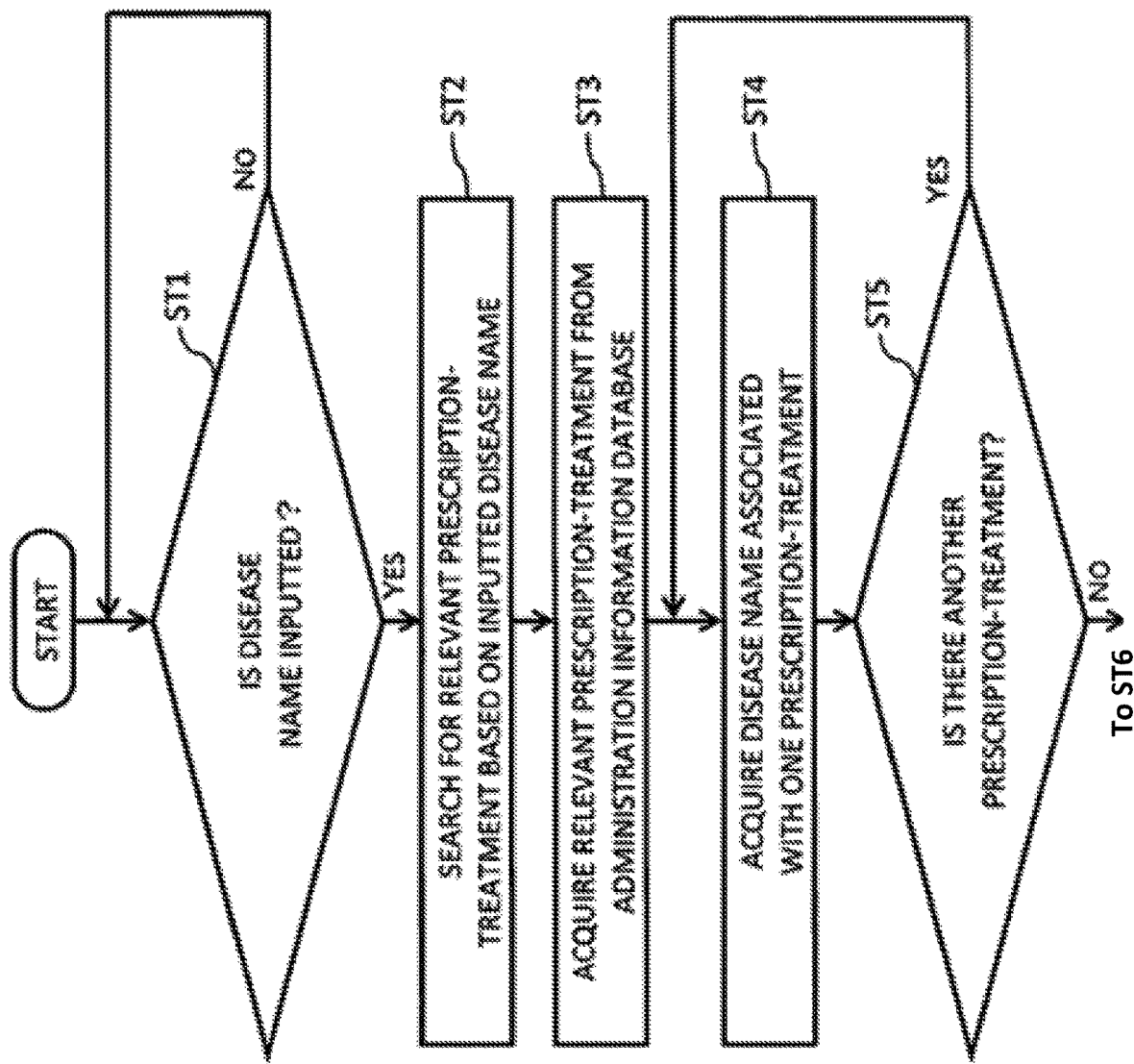
FIG. 9 is a flowchart illustrating a flow of search for electronic medical records by using a medical or health information search support apparatus in a first embodiment of the present invention.
Figure 9:
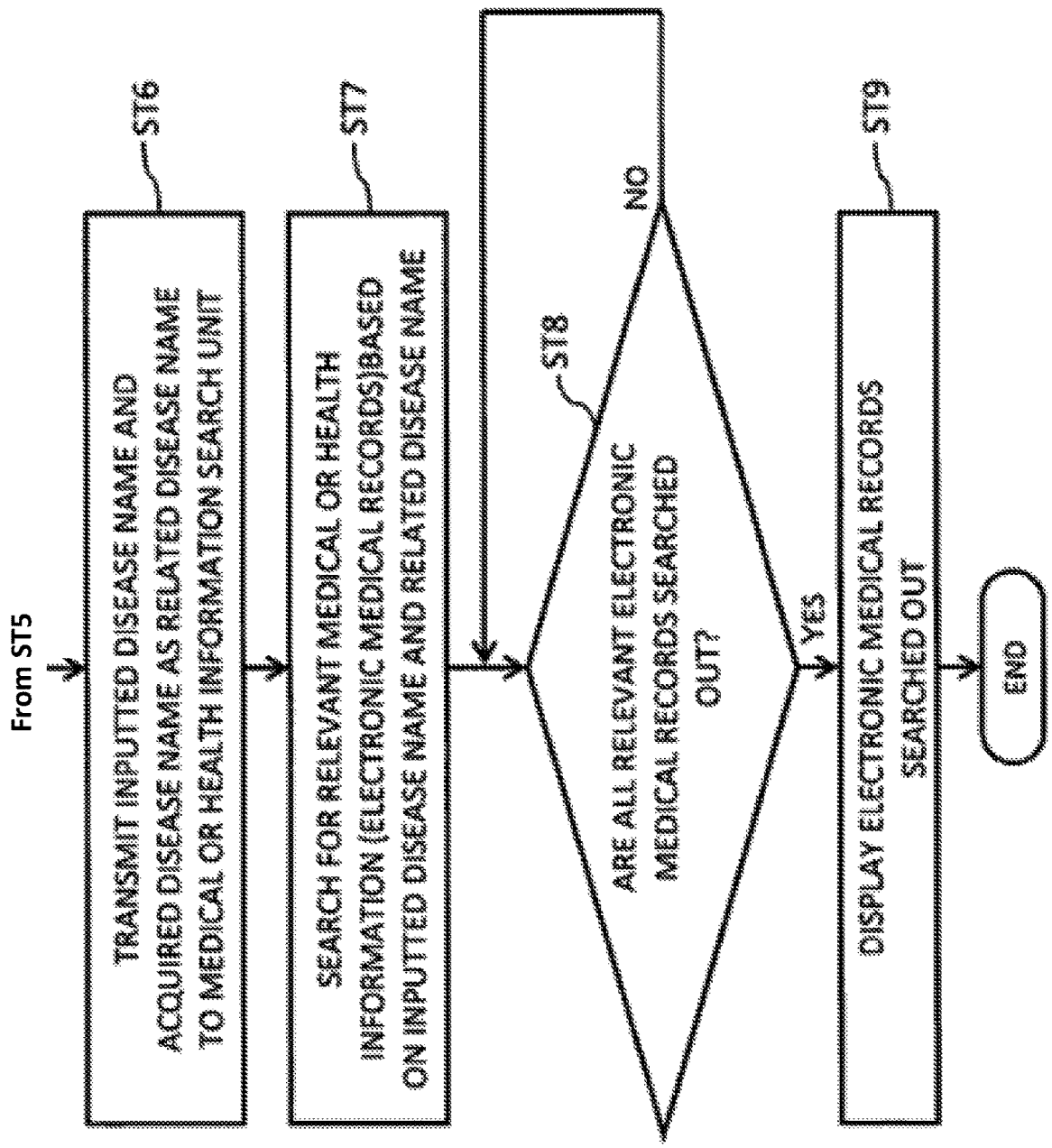

Next, with reference to FIGS. 9 and 10, description will be provided for a flow of search for electronic medical records by using the medical or health information search support apparatus 1. FIG. 9 is a flowchart illustrating a flow of searching for an electronic medical record by using a medical or health information search support apparatus 1 in a first embodiment of the present invention. FIG. 10 is an explanatory diagram illustrating the flow of search by using the structure of the administration information database 2 in the first embodiment of the present invention.

First of all, it is judged whether or not a user inputs a search keyword through the input unit 11 of the medical or health information search support apparatus 1 (ST1). The search keyword is a word entered in the electronic medical records of search target. Accordingly, the related disease name acquisition unit 12 stays on standby until a search keyword is inputted. Here, the description is given by taking an example in which the inputted search keyword is a disease name and the inputted disease name is also referred to a "main disease name" as needed.

Next, when it is judged that the disease name is inputted (YES in ST1), the related disease name acquisition unit 12 accesses the administration information database 2 via a communication controller, which is not illustrated but provided in the medical or health information search support apparatus 1, and the communication network N. The related disease name acquisition unit 12 accesses the administration information database 2 and searches for the relevant prescription-treatment based on the inputted disease name (main disease name) (ST2).

When the main disease name is, for example, "acute bronchitis," four prescriptions-treatments of "aaa granular medicine 50%," "fff tablet 15 mg," "ccc tablet 15 mg" and "granular bbb extract (for medical use)" are searched out and acquired (see FIG. 5) (ST3).

Then, the related disease name acquisition unit 12 searches the administration information database 2 based on one of the acquired prescriptions-treatments to find disease names provided with the prescription-treatment (ST4). For example, when the prescription-treatment is "aaa granular medicine 50%," "acute sinusitis" and "asthma" are cited as the disease names provided with "aaa granular medicine 50%" (see FIG. 5).

In other words, each prescription-treatment provided for a symptom of the inputted main disease name is identified based on the main disease name, and then a search is made based on the identified prescription-treatment to identify a disease name having a symptom provided with substantially the same prescription-treatment. Here, the disease name identified by search is referred to as a "related disease name" in relation to the main disease name.

FIG. 10 is the explanatory diagram illustrating the flow of search by using the structure of the administration information database 2 in the first embodiment of the present invention. As described above with reference to FIG. 5, when "acute bronchitis" is inputted as the search keyword, for example, the "prescriptions-treatments" associated with this disease name are identified. In the table illustrated in FIG. 10, four "prescriptions-treatments" are presented (specified). Then, the "prescriptions-treatments" associated with disease names different from the inputted search keyword are searched for the "prescription-treatment" matching each of the identified "prescriptions-treatments." Here, it can be understood that the prescription of "aaa granular medicine 50%" is also provided for "acute sinusitis," for example (see an arrow on the right side of the table). This is because the disease name of "acute sinusitis" and the prescription-treatment of "aaa granular medicine 50%" are associated with each other. In this way, the "related disease name" of "acute sinusitis" is searched out with regard to the main disease name of "acute bronchitis."

In the above example, prescriptions-treatments provided for the symptom of the disease name of "acute bronchitis" include three other prescriptions-treatments in addition to "aaa granular medicine 50%." Accordingly, with regard to each of these three prescriptions-treatments, a related disease name provided with substantially the same prescription-treatment is searched out and acquired in the same manner (ST5). Thus, the related disease names are searched out with regard to all the prescriptions-treatments provided for the main disease name.

The related disease names thus searched out are transmitted together with the firstly-inputted main disease name from the related disease name acquisition unit 12 to the medical or health information search unit 13 (ST6). Based on the main disease name and the related disease names thus received, the medical or health information search unit 13 accesses the medical or health information database 3 and searches for electronic medical records in each of which any of the main disease name and the related disease names is entered (ST7). Incidentally, the structure of the medical or health information database 3 may be any of the foregoing configurations.

When the medical or health information search unit 13 searches for electronic medical records on the related disease names, for example, in the medical or health information database 3 based on the main disease name and the related disease names, there is a case where an electronic medical record extracted in the search using the inputted main disease name as the search keyword is also extracted in the search based on any of the related disease names. In this case, the electronic medical record extracted based on the related disease name may be excluded. In this way, in terms of a relationship between the main disease name and the related disease name, how to handle an electronic medical record searched out based on the related disease name may be set as needed.

When two or more related disease names are extracted, the medical or health information search unit 13 has to search for electronic medical records on all the related disease names. For this reason, it is judged whether or not electronic medical records on all the received main disease name and related disease names are already searched out from the medical or health information database 3 (ST8). After that, the medical or health information search unit 13 causes the display unit 14 to display the electronic medical records thus acquired (ST9).

Figure 11:
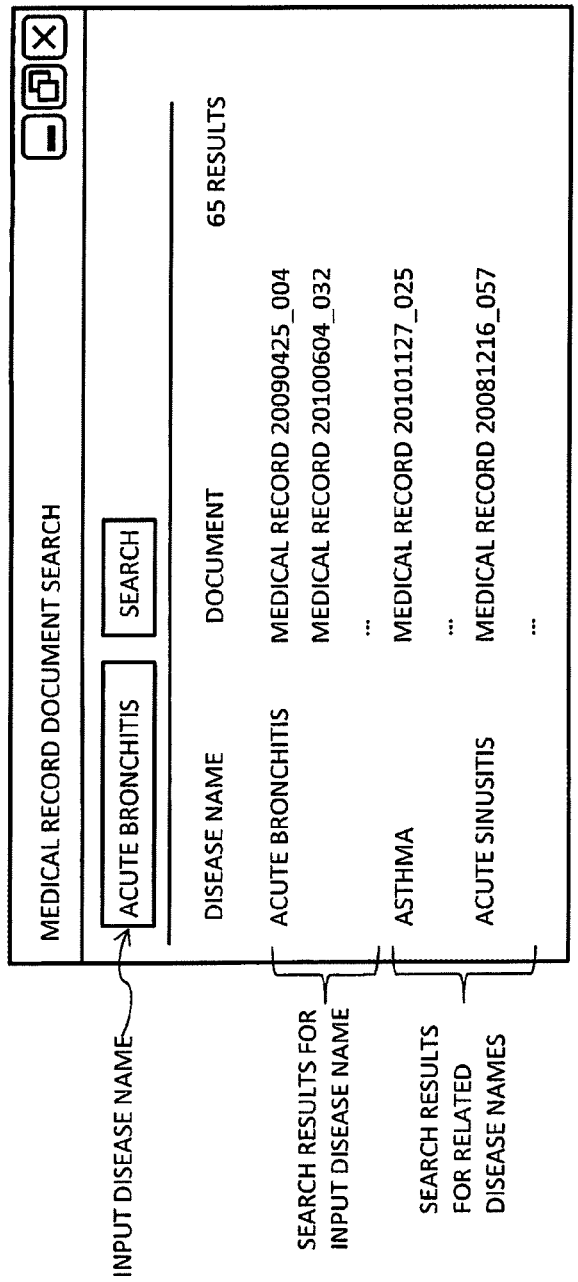
FIG. 11 is a screen example of the display unit on which electronic medical records each entered with the main disease name or one of the related disease names are searched out and displayed by a medical or health information search unit in the embodiment of the present invention.

FIG. 11 is a screen example of the display unit 14 on which electronic medical records each entered with the main disease name or one of the related disease names are searched out and displayed by the medical or health information search unit 13 in the embodiment of the present invention. The screen example in FIG. 11 is presented only for the illustrative purposes, and the layout, items to be displayed, and the like can be set as needed.

In the screen example presented in FIG. 11, a title named "MEDICAL RECORD DOCUMENT SEARCH" is displayed in the top position, and an input field for a user to input a disease name (main disease name) entered in electronic medical records that the user requires is provided immediately below the title. Then, when a "SEARCH" button provided beside the input field is pressed down, the aforementioned electronic medical record search processing is started. Here, for convenience of description, a main disease name is inputted in the input field of the main disease name unsurprisingly, but a prescription-treatment, for example, may be inputted in this field.

After completion of the search processing, information on the documents of electronic medical records in which the main disease name and the related disease names are entered is displayed. Here, totally 65 electronic medical records in each of which any of the main disease name and the related disease names is entered are searched out as search results. In addition, the "disease name" and "document" concerning the disease name are also displayed.

Moreover, the display unit 14 in the embodiment of the present invention displays search results for the main disease name which is an inputted disease name, and therebelow displays search results for the related disease names. With this way of display, the user can acquire all of the requisite electronic medical records and the electronic medical records on the related disease names. Incidentally, when a user selects a document number displayed on a "DOCUMENT" field, for example, the user is allowed to open the linked document.

By employing the configurations, the structures and the processing method described above, it is possible to provide a medical or health information search support apparatus and a medical or health information search support system which are capable of searching out not only a medical record entered with an inputted disease name (input disease name) but also medical records entered with other disease names (related disease names) provided with the same prescription-treatment as the prescription-treatment for the input disease name.

Even when somewhat-different expressions (variations) exist for an inputted main disease name, the processing in this way searches out a related disease name via the prescription-treatment identified from the inputted main disease name. Thus, it is possible to search out and display all of electronic medical records required by the user and electronic medical records related to the above electronic medical records without any omission. In addition, electronic medical records on not only an inputted main disease name but also its related disease names are searched out by use of the medical or health information search support system S in the embodiment of the present invention. Thus, it is possible to present, to a user such as a medical doctor, even electric medical records each not having an entry of a main disease name but involving a disease medically related to the main disease name. The processing in this way is very useful from the viewpoint of the secondary use of the electronic medical record system.

Moreover, mapping between multiple disease names (main disease names and related disease names) is established via prescriptions-treatments through the execution of the aforementioned search. Making an additional storage for storing the mapping eventually makes it possible to perform a search which requires just input of a main disease name and is capable of identifying a related disease name directly from the inputted main disease name without using the prescription-treatment.

Note that, the above search processing employs the method including searching, based on the prescription-treatment of the main disease name, for a related disease name provided with substantially the same prescription-treatment, and searching for the electronic medical records on the related disease name. Instead of this method, another method is also conceivable in which the related disease name acquisition unit 12 acquires information on prescriptions-treatments associated with a main disease name from the administration information database 2, and the medical or health information search unit 13 searches for electronic medical records from the medical or health information database 3 on the basis of the information of the prescriptions-treatments. In this case, the medical or health information database 3 can implement the method by forming a full-text search index of medical record documents in advance in terms of not "disease name" but "prescription-treatment" (see FIG. 4). This search processing method can skip a step of searching for a related disease name based on the prescription-treatment for the main disease name, and enables speed-up of the search by a time required by the skipped step.

Second Embodiment

Next, a second embodiment of the present invention will be described. In the second embodiment, the same constituents as the constituents described above in the first embodiment will be designated by the same reference numerals and duplicate explanation of the same constituents will be omitted herein.

The first embodiment of the present invention employs the method of performing a search based on the prescription-treatment of a main disease name to acquire a related disease name provided with substantially the same prescription-treatment, and then searching for electronic medical records on the acquired related disease name. In the second embodiment, description will be provided for a method in which, instead of a disease name, a prescription-treatment is inputted as a search keyword to search for desired electronic medical records.

Figure 12:
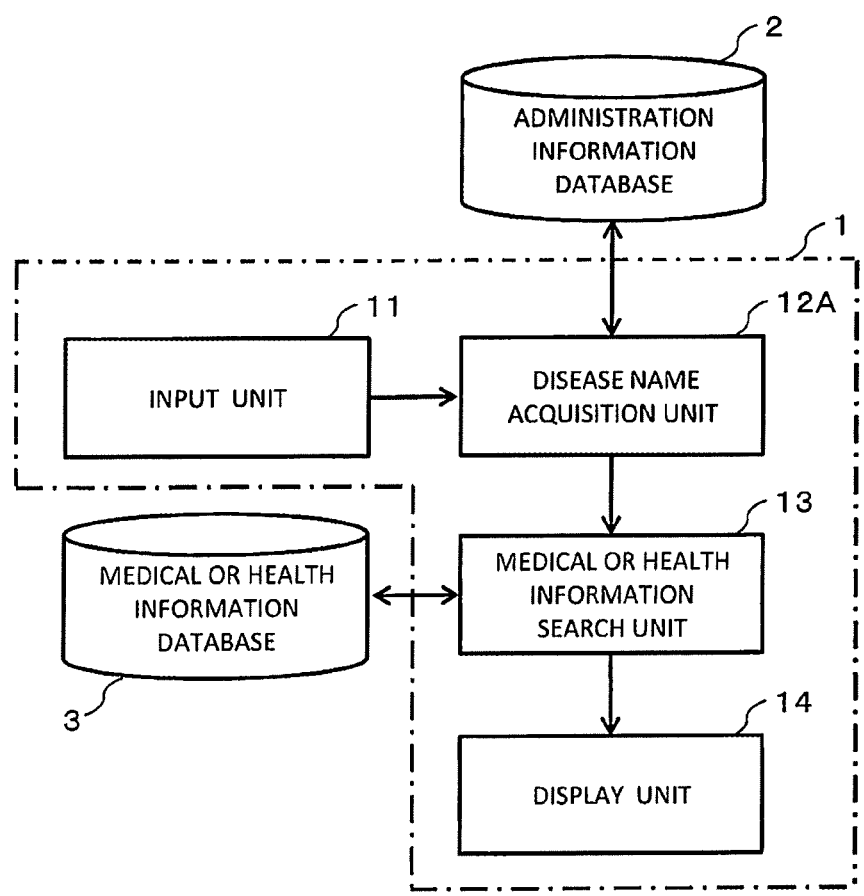
FIG. 12 is a block diagram illustrating an internal configuration of a medical or health information search support apparatus in a second embodiment of the present invention.

FIG. 12 is a block diagram illustrating an internal configuration of a medical or health information search support apparatus 1A in the second embodiment of the present invention. The medical or health information search support apparatus 1A has almost the same configuration as the medical or health information search support apparatus 1 in the first embodiment, but is different in a disease name acquisition unit 12A in the medical or health information search support apparatus 1A.

In the second embodiment, a prescription-treatment is inputted as the search keyword and desired electronic medical records are searched out eventually, as described above. Here, when the prescription-treatment is inputted as the search keyword, all the disease names provided with the inputted prescription-treatment are displayed on the display unit 14. In this case, the disease names provided with the same prescription-treatment are displayed without discrimination between the "main disease name" and the "related disease names."

A user selects a disease name relevant to a patient from the disease names displayed in response to the input of the prescription-treatment, and causes the medical or health information search unit 13 to search for medical or health information on the selected disease name. As a result, the electronic medical records thus searched out are displayed on the display unit 14, for example, as illustrated in FIG. 11.

Through the above way of search based on the prescription-treatment provided, disease names applicable to the patient can be listed up, and electronic medical records on each disease name considered relevant can be displayed by selecting the disease name. Hence, it is possible to provide a medical or health information search support apparatus and a medical or health information search support system which are capable of searching out medical records on multiple disease names without omission when a prescription-treatment is inputted.

In addition, even when somewhat-different expressions (variations) exist for an applied disease name, the disease names identified from the inputted prescription-treatment are searched out. Thus, it is possible to search out and display all of the electronic medical records required by the user and electronic medical records related to the above electronic medical records without omission.

Third Embodiment

Next, a third embodiment of the present invention will be described. In the third embodiment, the same constituents as the constituents described above in the first embodiment or the second embodiment will be designated by the same reference numerals and duplicate explanation of the same constituents will be omitted herein.

The third embodiment of the present invention is the same in the flow of searching out and displaying both of electronic medical records on an inputted main disease name, and electronic medical records on the related disease names without omission, which is described in the first embodiment. However, the third embodiment is embodied with the focus placed on in which order of related disease names to display their electronic medical records.

Figure 13:
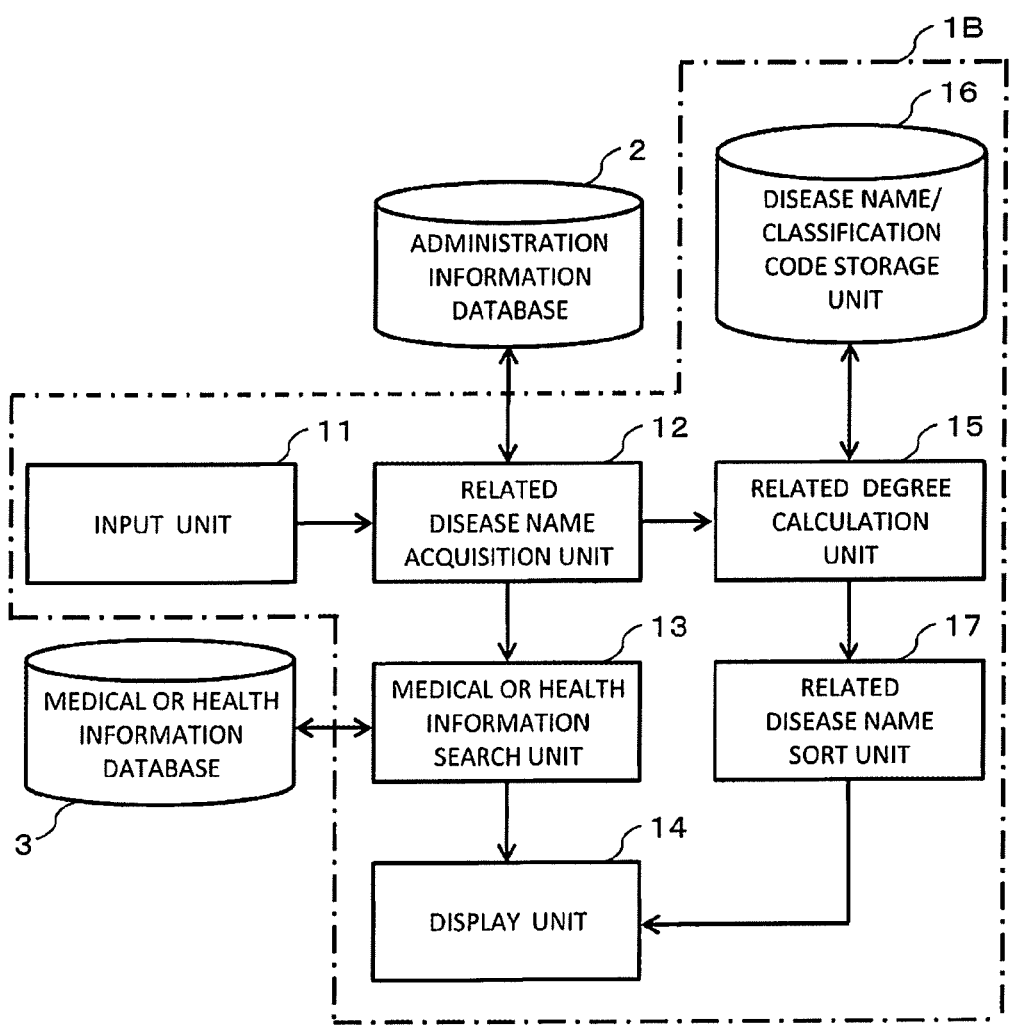
FIG. 13 is a block diagram illustrating an internal configuration of a medical or health information search support apparatus in a third embodiment of the present invention.

FIG. 13 is a block diagram illustrating an internal configuration of a medical or health information search support apparatus 1B in the third embodiment of the present invention. The medical or health information search support apparatus 1B has the same basic configuration as the medical or health information search support apparatus 1 in the first embodiment. However, the medical or health information search support apparatus 1B in the third embodiment newly and additionally includes a related degree calculation unit 15, a disease name/classification code storage unit 16 and a related disease name sort unit 17.

The related degree calculation unit 15 calculates how much a related disease name extracted via a prescription-treatment provided for a main disease name is related to the main disease name. In other words, the related degree calculation unit 15 calculates a distance of the related disease name from the main disease name. Here, a related degree of the related disease name to the main disease name is calculated by use of classification codes assigned to respective disease names, which will be described below in detail.

The disease name/classification code storage unit 16 stores classification codes assigned to the respective disease names. Here, any kind of code can be used as "classification code." The third embodiment of the present invention uses, for example, the international classification for statistical standards named ICD10. Here, "ICD10" is "the 10th revision of the International Statistical Classification of Diseases and Related Health Problems (a popular name, International Classification of Disease)" and is classification published as international statistical standards for death causes and diseases by World Health Organization (WHO). In the classification of this ICD10, diseases having a close relationship are assigned classification codes close to each other. To put it the other way around, a related degree between disease names becomes greater as the values of the classification codes thereof become closer to each other.

FIG. 14 is a table presenting a relationship between a classification code and a disease name stored in the disease name/classification code storage unit 16 in the third embodiment of the present invention. The information is stored for each disease name ID in the disease name/classification code storage unit 16. According to this table, it can be understood that "acute bronchitis" and "acute bronchiolitis," for example, are diseases having a close relationship with each other because their classification codes are "1020" and "1021." Thus, the two can be said to be diseases having a high related degree therebetween. On the other hand, it is considered that "acute bronchitis" has a closer relationship with "acute sinusitis" having a classification code "1001" than with "asthma" having a classification code "1045."

In the above way, the related degree between the main disease name and the related disease name is judged by using the classification such as ICD10, for example.

The related disease name sort unit 17 determines an order of search-out related disease names in display of electronic medical records on the basis of the related degree between the main disease name and each of the related disease names judged by the related degree calculation unit 15. Here, the electronic medical records on the related disease names are usually displayed in descending order of the related degree with the main disease name. However, the electronic medical records on the related disease names can be also displayed in ascending order of the related degree with the main disease name. Thus, the order can be set as needed.

Figure 15:
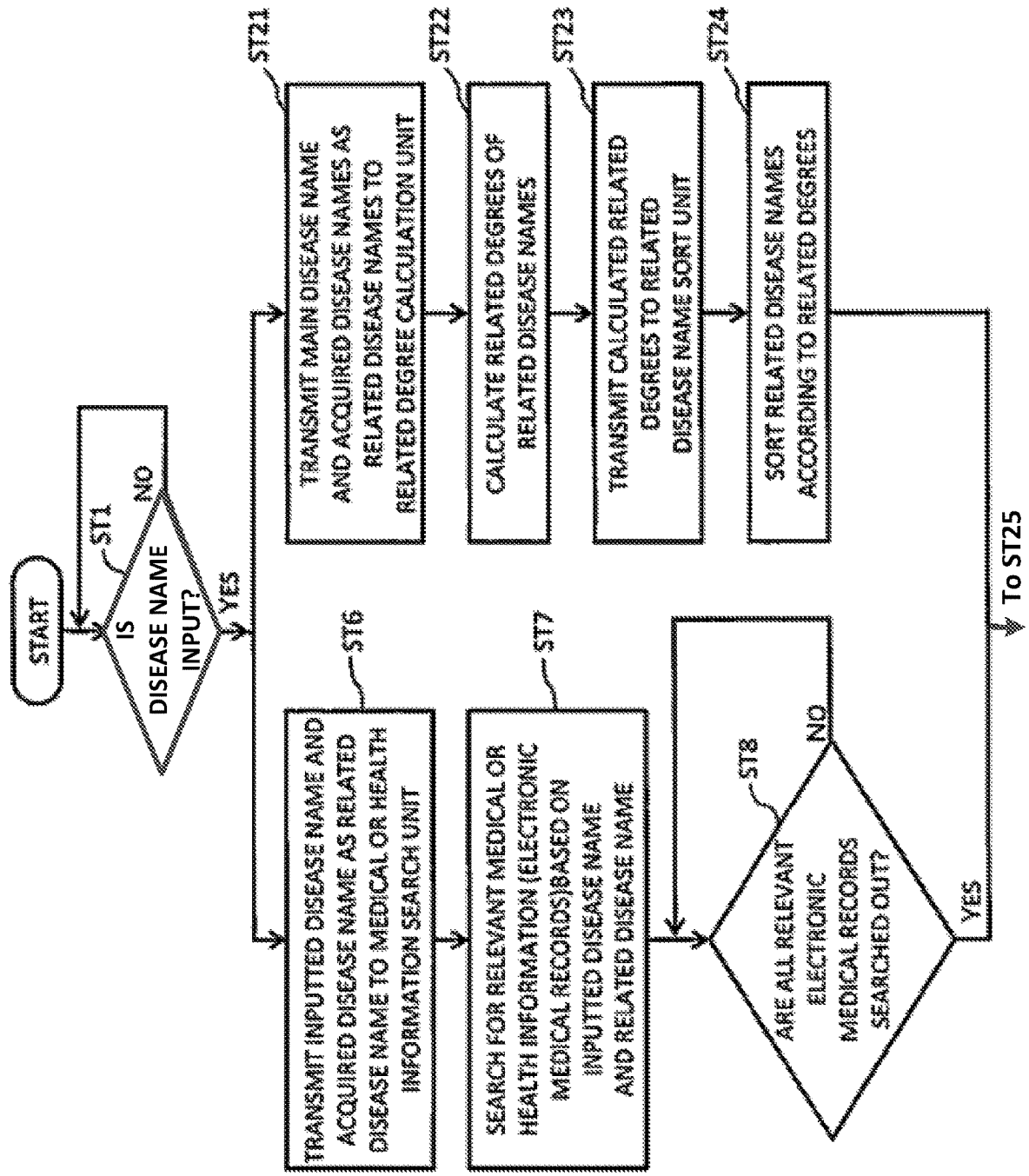
FIG. 15 is a flowchart illustrating a flow of determining an order of related disease names in display of their electronic medical records in the third embodiment of the present invention.
Figure 15:
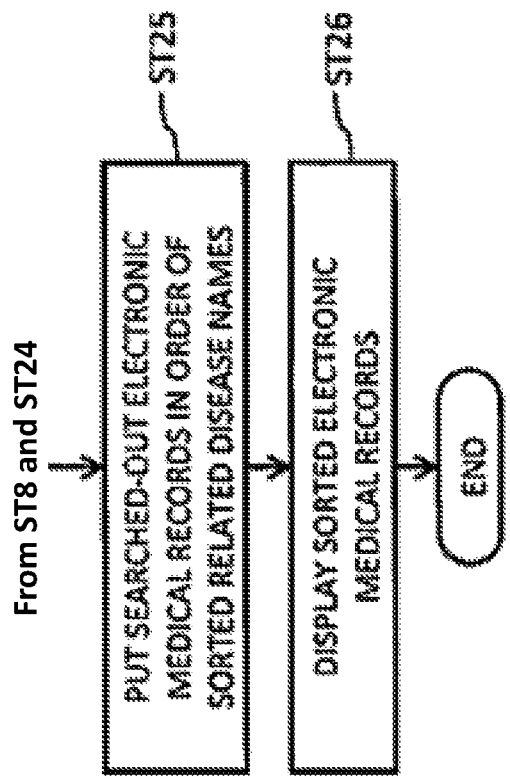

FIG. 15 is a flowchart illustrating a flow of determining an order of related disease names in display of electronic medical records in the third embodiment of the present invention. Part of the flow (steps ST1 to ST5) after a user of the medical or health information search support apparatus 1B inputs a main disease name until related disease names are acquired is the same as that described in the first embodiment (see FIG. 9). (Steps ST2 to ST5 are omitted in FIG. 15.)

Moreover, part of the flow in which the main disease name and the related disease names are transmitted to the medical or health information search unit 13, and the medical or health information search unit 13 searches for the relevant electronic medical records in the medical or health information database 3 based on the transmitted information is also the same as that described above (see steps ST6 to ST8 in FIG. 15). In parallel to the above search processing, however, the third embodiment executes processing of calculating a related degree between the main disease name and each of the searched-out related disease names for determining the order of the related disease names in display of electronic medical records.

Specifically, as illustrated in the flowchart in FIG. 15, the related disease name acquisition unit 12 sends the related degree calculation unit 15 the main disease name and the related disease names extracted via the prescription-treatment provided for the main disease name (ST21). The related degree calculation unit 15 having received the main disease name and the related disease names accesses the disease name/classification code storage unit 16 and acquires the classification codes of the respective disease names. After that, the related degree calculation unit 15 calculates the related degree of each related disease name with the main disease name (ST22). In the calculation of the related degree, how close the related disease name is to the main disease name is judged by use of the classification codes assigned to the respective disease names as described above. For example, when "acute bronchiolitis" and "asthma" are identified as related disease names of the main disease name of "acute bronchitis," "acute bronchiolitis" having the classification code "1021" is judged as being closer to the main disease name of "acute bronchitis" having the classification code "1020" than "asthma" having the classification code "1045" is.

The related degree calculation unit 15 transmits the calculated related degrees to the related disease name sort unit 17 (ST23). Here, for example, the absolute value of a difference between the classification codes of the main disease name and the related disease name can be recognized as a "related degree" and the difference is transmitted to the related disease name sort unit 17. It should be noted that the method of using the classification codes to calculate the related degrees is not limited to the aforementioned method.

The related disease name sort unit 17 having received the related degrees sorts the related disease names according to the related degrees (ST24). After that, the related disease name sort unit 17 puts the electronic medical records of the related disease names in the sorted order (ST25), and causes the display unit 14 to display the electronic medical records in the sorted order (ST26).

By employing the configurations, the structures and the processing method described above, it is possible to provide a medical or health information search support apparatus and a medical or health information search support system which are capable of searching out both of medical records entered with an inputted disease name (input disease name) and medical records entered with other disease names (related disease names) provided with the same prescription-treatment as the prescription-treatment for the input disease name.

In particular, it is possible to provide a medical or health information search support system very convenient to users because the electronic medical records on related disease names are displayed in the order started from the related disease name having the closest relationship (the highest related degree) with the inputted main disease name.

Although the third embodiment has been described on the assumption that the processing of calculating the related degrees between the main disease name and the related disease names is performed in parallel to the search processing of electronic medical records, the related degree calculation processing may be performed after the search processing, for example, in another employable flow.

Fourth Embodiment

Next, a fourth embodiment of the present invention will be described. In the fourth embodiment, the same constituents as the constituents described above in the first embodiment through the third embodiment will be designated by the same reference numerals and duplicate explanation of the same constituents will be omitted herein.

In the fourth embodiment, a range (display level) of related disease names is set to cause the display unit 14 to display electronic medical records on extracted related disease names, and the electronic medical records on the related disease names within the set range are displayed.

Figure 16:
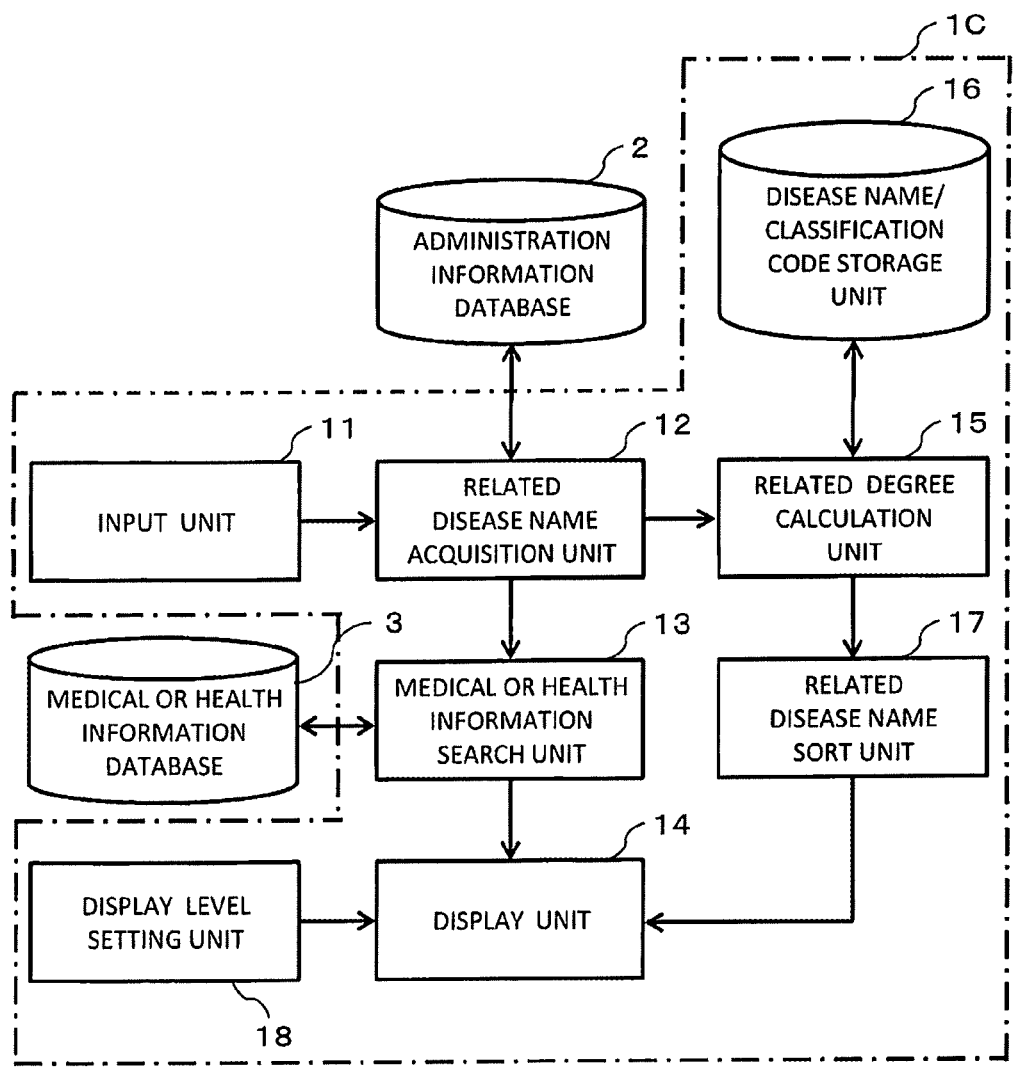
FIG. 16 is a block diagram illustrating an internal configuration of a medical or health information search support apparatus in a fourth embodiment of the present invention.

FIG. 16 is a block diagram illustrating an internal configuration of a medical or health information search support apparatus 1C in the fourth embodiment of the present invention. The medical or health information search support apparatus 1C in the fourth embodiment of the present invention has almost the same internal configuration as the medical or health information search support apparatus 1B in the third embodiment, but is different in that a display level setting unit 18 is provided therein.

The display level setting unit 18 sets a level indicating in which range of related disease names the display unit 14 is to display electronic medical records. Note that the level may be set in advance before a search, or after the search results are displayed, the level may be set on a screen in which the electronic medical records on the related disease names are displayed.

In the level setting, levels "1" and "2" may be set, for example, such that one or more electronic medical records per level may be displayed in descending order of the related degree with the main disease name. Alternatively, the electronic medical records on the main disease name and one related disease name may be always displayed by the display unit 14, and a "level 1" may be set as a mode of displaying electronic medical records on two related disease names, for example.

Figure 17:
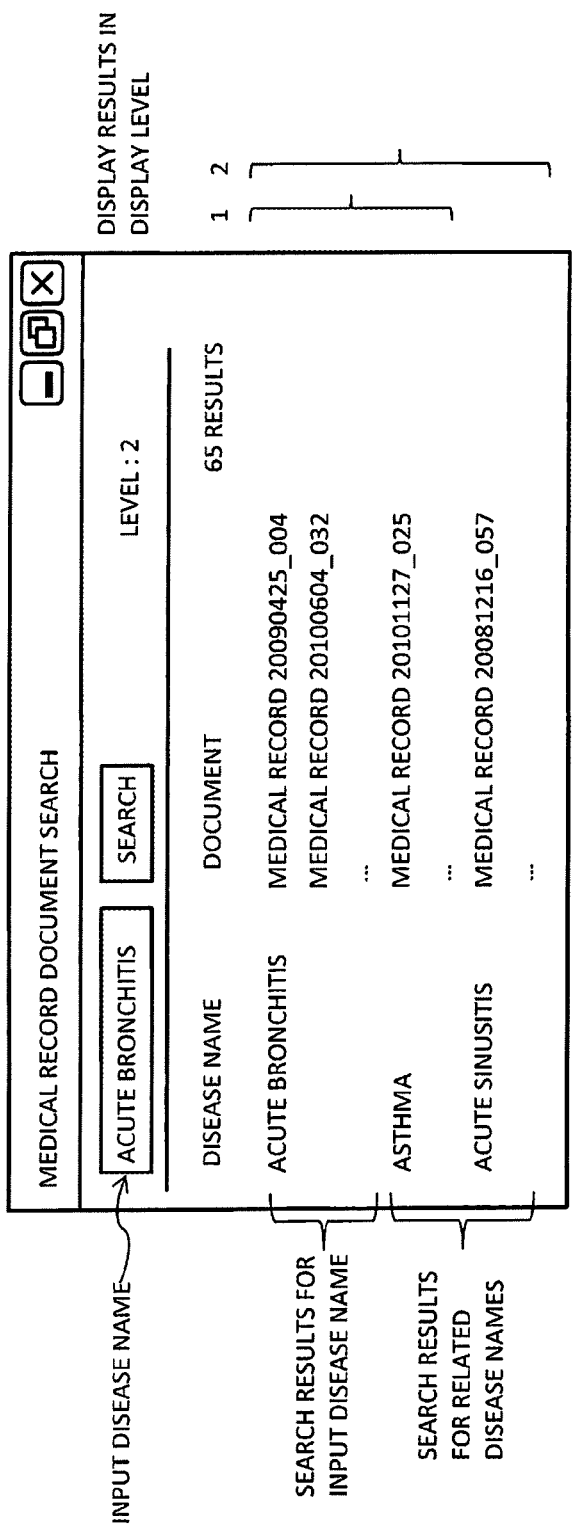
FIG. 17 is a screen example illustrating a display unit in which a display level is set in the fourth embodiment of the present invention.

FIG. 17 is a screen example illustrating the display unit 14 in which the display level is set in the fourth embodiment of the present invention. The basic display layout is the same as the layout of the display unit 14 illustrated in FIG. 11. In this screen example, "DISPLAY LEVEL: 2" is displayed on the right side of the field of the input disease name. In addition to the information on the electronic medical records on the inputted main disease name, the information on the electronic medical records on two related disease names in descending order of the related degree. In this case, "DISPLAY LEVEL: 1" is set as a mode of displaying electronic medical records on one related disease name. Accordingly, the level of display at the "DISPLAY LEVEL: 2" is a mode of displaying electronic medical records on related disease names having the first and second highest related degrees with the main disease name.

By employing the configurations, the structures and the processing method described above, it is possible to provide a medical or health information search support apparatus and a medical or health information search support system which are capable of searching out both of medical records entered with an inputted disease name (input disease name) and medical records entered with other disease names (related disease names) provided with the same prescription-treatment as the prescription-treatment for the input disease name.

In particular, when a large number of electronic medical records on the main disease name or the related disease names are searched out, the display of the electronic medical records can be delimited by any of the disease names. Thus, for a user who does not require the display of all the huge number of electronic medical records, it is possible to display electronic medical records only within a range appropriate for use. This leads to improvements in the convenience and efficiency of electronic medical records.

Fifth Embodiment

Next, a fifth embodiment of the present invention will be described. In the fifth embodiment, the same constituents as the constituents described above in the first embodiment through the fourth embodiment will be designated by the same reference numerals and duplicate explanation of the same constituents will be omitted herein.

The first to fourth embodiments described so far are provided on the assumption that a user searches for necessary electronic medical records by using the medical or health information search support apparatus 1. The fifth embodiment is characterized in that such functions of the medical or health information search support apparatus 1 are installed in a search server 7 connected to a communication network N; and that an information terminal 8 operated by a user is a device only having functions to make a search request for electronic medical records to the search server 7 and to receive and display search results obtained by the search server 7.

The provision of such functions to the search server 7 and the information terminal 8 enables employment of a network system such as a thin client system or cloud system, for example.

Figure 18:
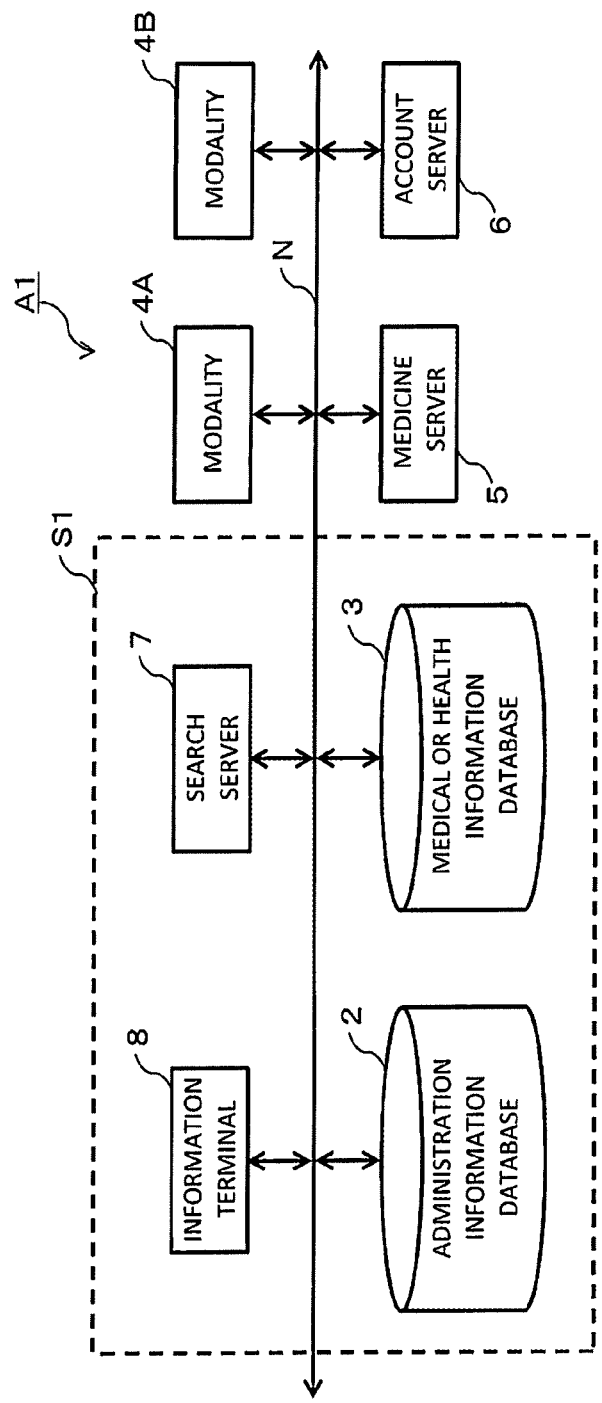
FIG. 18 is a block diagram illustrating an overall configuration of an in-hospital system in a fifth embodiment.

FIG. 18 is a block diagram illustrating an overall configuration of an in-hospital system A1 in the fifth embodiment. As illustrated in FIG. 18, a medical or health information search support system S1, modalities 4, a medicine server 5 and an account server 6 are connected to the communication network N. Then, the medical or health information search support system S1 includes an administration information database 2, a medical or health information database 3, the search server 7 and the information terminal 8. Among these constituents, the administration information database 2 and the medical or health information database 3 are the same as the administration information database 2 and the medical or health information database 3 in the first to fourth embodiments described above.

Figure 19:
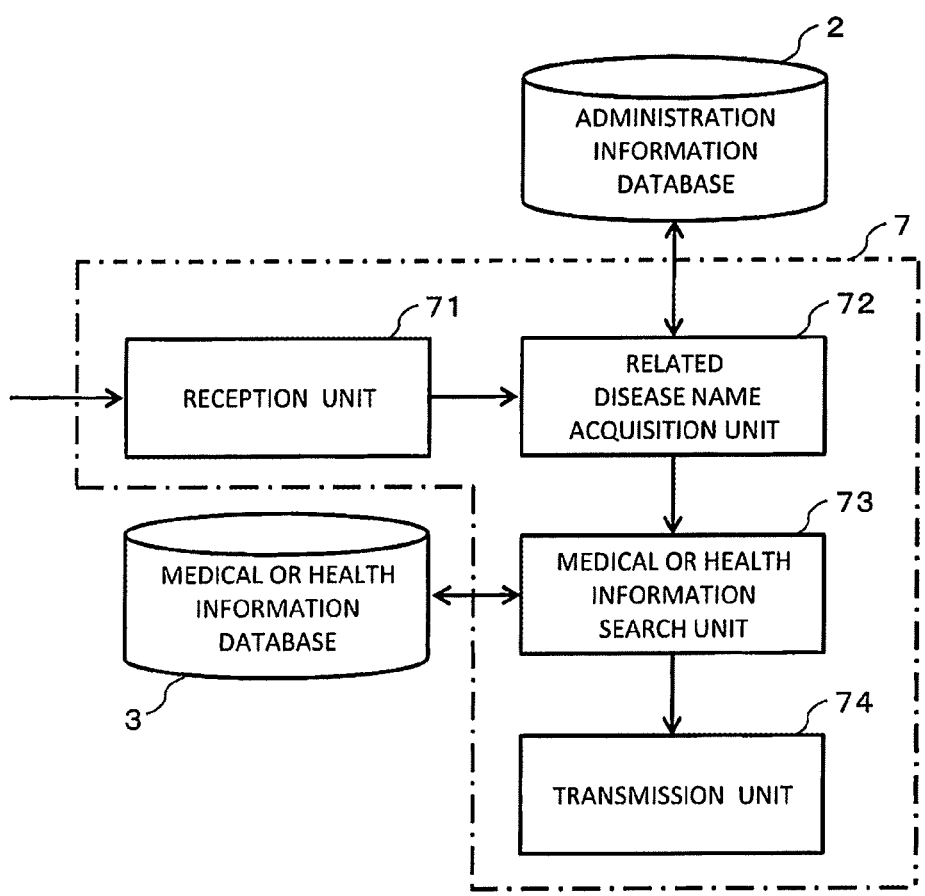
FIG. 19 is a block diagram illustrating an internal configuration of a search server in the fifth embodiment of the present invention.

FIG. 19 is a block diagram illustrating an internal configuration of the search server 7 in the fifth embodiment. The search server 7 includes a reception unit 71, a related disease name acquisition unit 72, a medical or health information search unit 73 and a transmission unit 74.

The reception unit 71 receives a search request for electronic medical records from the information terminal 8. On the basis of a disease name (main disease name) inputted on the information terminal 8, the related disease name acquisition unit 72 accesses the administration information database 2 and identifies prescription-treatments provided for the main disease name. Then, the related disease name acquisition unit 72 acquires related disease names having disease names different from the main disease name and being provided with each of the identified prescription-treatments. The related disease names thus acquired are transmitted to the medical or health information search unit 73.

The medical or health information search unit 73 accesses the medical or health information database 3 and searches for electronic medical records in which the main disease name and the related disease names are entered. Information on the searched-out electronic medical records is transmitted via the transmission unit 74 to the information terminal 8 having made the search request. The information terminal 8 having received the information on the electronic medical records displays the electronic medical records on the main disease name and the electronic medical records on the related disease names on a display unit as illustrated in FIG. 8, for example.

The information terminal 8 in the fifth embodiment makes a search request for desired electronic medical records to the search server 7 and displays searched-out electronic medical records, as described above. Accordingly, the information terminal 8 only has to include at least an input unit, for example, needed to make a search request to the search server 7 and a display unit to display the searched-out electronic medical records. As a matter of course, the information terminal 8 includes constituents necessary to function as the information terminal 8, such as a CPU and a communication controller for connecting to the communication network N, for example. Incidentally, only one information terminal 8 is connected to the communication network N in FIG. 18, but any number of information terminals 8 may be connected to the communication network N.

Although the search server 7 has the functions to search out the electronic medical records based on the search request from the information terminal 8 and to cause the searched-out electronic medical records to be displayed, the search server 7 may additionally have a function to cause related disease names to be displayed in descending order of the related degree with the main disease name, for example, a function to cause the display in accordance with a predetermined display level, for example, and any other functions.

By employing the configurations, the structures and the processing method described above, it is possible to provide a medical or health information search support apparatus and a medical or health information search support system which are capable of searching out both of medical records entered with an inputted disease name (input disease name) and medical records entered with other disease names (related disease names) provided with the same prescription-treatment as the prescription-treatment for the input disease name.

In particular, since the processing for searching for electronic medical records is centrally performed in the search server 7, the information terminal 8 only has to have at least a function to make a search request to the search server 7 and a function to receive search results obtained by the search server 7. This means that the centralization of the search processing in the search server 7 enables an information terminal to operate without having the search function. Thus, in order to build an in-house system, this configuration can be very advantageous in costs while achieving the same-level of efficiency in the search processing, in comparison with a case where information terminals having a function to search for electronic medical records need to be installed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions.

For example, in the foregoing embodiments of the present invention, the inputted disease name is treated as starting information of the medical or health information search. The inputted information, however, may be other kinds of information such as "a symptom" or "a disease name containing inputted text." What kind of information is to be inputted by a user of the medical or health information search support system can be set as needed.

The accompanying claims and their equivalents are intended to cover such forms or modifications as would fall within the scope and spirit of the inventions.

What is claimed is:

1. A medical or health information search support apparatus comprising:
    an input device to which a search keyword for searching for medical or health information of search target is inputted; processing circuitry configured to
        search an administration information database that stores administration information by the search keyword, the administration information including respective prescription-treatments for respective patients, and each of the prescription-treatments being associated with a disease name for which the prescription-treatment was prescribed, and acquire related disease names for the search keyword based on a degree of relatedness between the disease names in the administration information, the degree of relatedness being obtained using a numerical difference between values of classification codes; and
        search for medical or health information stored in a medical or health information database on the basis of the search keyword and a related disease name that is related to the search keyword based on the degree of relatedness; and
    a display configured to display the medical or health information thus searched out, wherein,
    the processing circuitry is further configured to determine a display level indicating a range of related disease names to be displayed by the display among the generated related disease names based on the degree of relatedness, the display level being selected from a first display level and a second display level, the first display level including the related disease names for which numerical differences between a value of a classification code of the search keyword and respective values of classification codes of the related disease names are below a first threshold, and the second display level including the related disease names for which numerical differences between the value of the classification code of the search keyword and the respective values of the classification codes of the related disease names are below a second threshold, wherein the first threshold is greater than the second threshold,
    the display displays the acquired medical or health information of the related disease names as well as the medical or health information of the search keyword, and
    when a disease name is input as the search keyword, the degree of relatedness used to determine the related disease name is based on a prescription-treatment of the related disease being substantially the same as the prescription treatment associated with the disease name inputted as the search keyword.

2. The medical or health information search support apparatus according to claim 1, wherein the processing circuitry is further configured to output, as search results, plural pieces of medical or health information containing the related disease name, related to the disease name contained in the medical or health information searched out based on the search keyword.

3. The medical or health information search support apparatus according to claim 1, wherein the search keyword for searching for the medical or health information is any one of the disease name, the related disease name, and the prescription-treatment.

4. The medical or health information search support apparatus according to claim 2, wherein the search keyword for searching for the medical or health information is any one of the disease name, the related disease name, and the prescription-treatment.

5. The medical or health information search support apparatus according to claim 1, wherein when the medical information searched out based on the disease name and the medical or health information searched out based on the related disease name are the same medical or health information, the processing circuitry deletes the medical or health information searched out based on the related disease name.

6. The medical or health information search support apparatus according to claim 1, wherein the medical or health information database accessed by the processing circuitry stores therein a full text entered in an electronic medical record containing information on a patient and further stores therein an index used in searching for the medical or health information in association with a particular kind of information.

7. The medical or health information search support apparatus according to claim 1, wherein the processing circuitry is further configured to:
    calculate the degree of relatedness of each related disease name with respect to the disease name inputted as the search keyword to generate related degrees,
    sort the each related disease names in a display order on the basis of the generated related degrees, and
    the medical or health information search support apparatus further comprises a disease name/classification code memory configured to store each disease name and a classification code for use to calculate the degree of relatedness, in association with each other.

8. The medical or health information search support apparatus according to claim 7, wherein the processing circuitry is further configured to calculate the degree of relatedness of the related disease name with a disease name inputted as the search keyword on the basis of a difference between the classification codes of the inputted disease name and related disease names stored in the disease name/classification code memory.

9. A medical or health information search support system comprising:
an administration information database in which administration information is stored, the administration information including respective prescription-treatments for respective patients, and each of the prescription-treatments being associated with a disease name for which the prescription-treatment was prescribed;
a medical or health information database in which medical or health information on the patient is stored; and
a medical or health information search support apparatus including:
an input device to which a search keyword for searching for medical or health information of search target is inputted,
processing circuitry configured to
search the administration information database by the search keyword, and acquire related disease names for the search keyword based on a degree of relatedness between the disease names in the administration information obtained using a numerical difference between values of the classification codes, and
search for medical or health information stored in the medical or health information database on the basis of the search keyword and a related disease name that is related to the search keyword based on the degree of relatedness, and
a display configured to display the medical or health information thus searched out, wherein
the processing circuitry is further configured to determine a display level indicating a range of related disease names to be displayed by the display among the generated related disease names based on the degree of relatedness, the display level being selected from a first display level and a second display level, the first display level including the related disease names for which numerical differences between a value of a classification code of the search keyword and respective values of classification codes of the related disease names are below a first threshold, and the second display level including the related disease names for which numerical differences between the value of the classification code of the search keyword and the respective values of the classification codes of the related disease names are below a second threshold, wherein the first threshold is greater than the second threshold,
the display displays the acquired medical or health information of the related disease names as well as the medical or health information of the search keyword, and
when a disease name is input as the search keyword, the degree of relatedness used to determine the related disease name is based on a prescription-treatment of the related disease being substantially the same as the prescription treatment associated with the disease name inputted as the search keyword.

10. The medical or health information search support system according to claim 9, wherein the processing circuitry is further configured to:

calculate the degree of relatedness of each related disease name with respect to the disease name inputted as the search keyword to generate related degrees,
sort the related disease names in a display order on the basis of the generated related degrees, and
the medical or health information search support system further comprises a disease name/classification code memory configured to store each disease name and a classification code for use to calculate the degree of relatedness, in association with each other.

11. A medical or health information search support system, comprising:
an information terminal used by a person who refers to medical or health information, and at least including an input device and a display;
an administration information database in which administration information is stored, the administration information including respective prescription-treatments for respective patients, and each of the prescription-treatments being associated with a disease name for which the prescription-treatment was prescribed
a medical or health information database in which medical or health information on the patient is stored; and
a search server including processing circuitry configured to:
receive a search request for medical or health information of a search target from the information terminal,
search the administration information database by the search keyword, and acquire related disease names for the search keyword based on a degree of relatedness between the disease names in the administration information obtained using a numerical difference between values of the classification codes,
search for medical or health information stored in the medical or health information database on the basis of a search keyword of the received search request and the related disease name to obtain a searched-out medical or health information, and
transmit the searched-out medical or health information to the information terminal, wherein
the processing circuitry is further configured to determine a display level indicating a range of related disease names to be displayed by the display of the information terminal among the generated related disease names based on the degree of relatedness, the display level being selected from a first display level and a second display level, the first display level including the related disease names for which numerical differences between a value of a classification code of the search keyword and respective values of classification codes of the related disease names are below a first threshold, and the second display level including the related disease names for which numerical differences between the value of the classification code of the search keyword and the respective values of the classification codes of the related disease names are below a second threshold, wherein the first threshold is greater than the second threshold, and
the degree of relatedness used to determine the related disease name is based on a prescription-treatment of the related disease being substantially the same as the prescription treatment associated with the disease name inputted in the information terminal as part of the search request.

12. The medical or health information search support system according to claim 11, wherein the processing circuitry is further configured to:

calculate a respective degree of relatedness of each of a plurality of related disease names with respect to the disease name to generate related degrees; and sort the plurality of related disease names in a display order on the basis of the related degrees, and the medical or health information search support system further comprises a disease name/classification code memory configured to store each disease name and a classification code for use to calculate the degree of relatedness, in association with each other.

13. The medical or health information search support system according to claim 11, wherein the search keyword is one or more of the disease name, the related disease name, and a prescription-treatment prescribed for the disease name.

* * * * *